United States Patent [19]

Montagnier et al.

[11] Patent Number: 5,221,610
[45] Date of Patent: Jun. 22, 1993

[54] DIAGNOSTIC METHOD AND COMPOSITION FOR EARLY DETECTION OF HIV INFECTION

[75] Inventors: Luc Montagnier, Robinson; Herve Rochat, Minet; El M. Bahraoui, Cacheu; Solange Chamaret; Stephane Ferris, both of Paris; Claude Granier, Hameau Saint-Felix; Jurphaar V. Rietschoten, AIX-EN-Provence; Jean-Marc Sabatier, Marseilles, all of France

[73] Assignees: Institut Pasteur; Institut National de la Sante et de la Recherche Medicale; Centre National de la Recherche Scientifique, Paris, France

[21] Appl. No.: 754,300

[22] Filed: Sep. 4, 1991

Related U.S. Application Data

[63] Continuation of Ser. No. 199,143, May 26, 1988.

[51] Int. Cl.$^5$ ............................................. G01N 33/53
[52] U.S. Cl. ..................................... 435/7.1; 435/7.92; 435/974; 530/350
[58] Field of Search ................. 530/350; 435/7.1, 7.92, 435/974

[56] References Cited

FOREIGN PATENT DOCUMENTS 2600079 12/1987 France .
WO91/04051 4/1991 PCT Int'l Appl. .

OTHER PUBLICATIONS

Mireille Guyader, Nature 326:662–669 (1987).
Bruno Guy et al., Nature 330:266–269 (1987).
Wain–Hobson et al., Cell, 40:9–17 (1985).
Allan et al., Science, 230:810–813 (1985).
Arya et al., Proc. Natl. Acad. Sci. USA, 83:2209–2213 (1986).
Terwilliger et al., J. Virol., 60:754–760 (1986).
Luciw et al., Proc. Natl. Acad. Sci. USA, 84:1434–1438 (1987).
Samuel et al, "The 3'–orf protein of human immunodeficiency virus shows structural homology with the phosphorylation domain site of the protein kinase family," FEBS Lett. 218 (Jun. 22, 1987) 81–86.

*Primary Examiner*—Christine M. Nucker
*Attorney, Agent, or Firm*—Finnegan, Henderson, Farabow, Garrett & Dunner

[57] ABSTRACT

Polypeptides encoded by the nef gene of Human Immunodeficiency Virus (HIV), which is the major etiological agent of Acquired Immune Deficiency Syndrome (AIDS), are identified. The polypeptides, a diagnostic method for detecting antibodies to HIV in biological fluids, a diagnostic kit for carrying out the method, and pharmaceutical compositions containing the polypeptides are described. The polypeptides are useful in viral vaccines and for the early detection of HIV infection in humans.

5 Claims, 4 Drawing Sheets

```
         10        20        30             40        50
MGASGSKKHSRPPRGLQERLLRARAGACGGYWNESG--G-----EYSRFQEGSDREQKSP    HIV2
                               ::  :  :       :  :
                               MGGKWSKSSVVGWPTVRERMRRAEPAADGVGAA HIV1
                                      10        20        30

60        70              80        90       100
SCEGRQYQQGDFMNTPWKDPAA-------EREKNLYRQQNMDDVDSDDDDQVRVSVTPKV   HIV-2
 :        ::                   :  :                  :  ::: :
SRDLEKHGAITSSNTAATNAACAWLEAQEE-EE-------------------VGFPVTPQV HIV-1
        40        50        60                              70

110       120       130       140       150       160
PLRPMTHRLAIDMSHLIKTRGGLEGMFYSERRHKILNIYLEKEEGIIADWQNYTHGPGVR   HIV-2
::::::      :   : ::      ::::::    : ::   ::          ::::::    :::::
PLRPMTYKAAVDLSHFLKEKGGLEGLISHQRRQDILDLWIYHTQGYFPDWQNYTPGPGVR   HIV-1
        80        90       100       110       120       130

170       180       190       200       210  .    220
YPMFFGWLWKLVPV--DVPQEGEDTETHCLVHPAQTSKFDDPHGETLVWEFDPLLAYSYE   HIV2
::  :::  :::::    :    :    :  ::      ::     : :  : ::   ::
YPLTFGWCYKLVPVEPDKVEEANKGENTSLLHPVSLHGMDDPEREVLEWRFDSRLAFHHV   HIV1
       140       150       160       170       180       190

230       240       250
AFIRYPEEFGHKSGLPEEEWKARLKARGIPFS
 :        :: :
ARELHPEYFKNC
       200
```

FIGURE 2

| Protected function | Protective group | |
|---|---|---|
| OH of tyrosine | 2,6-dichlorobenzyl | $-CH_2-\underset{Cl}{\underset{|}{\overset{Cl}{\overset{|}{C_6H_3}}}}$ |
| OH of threonine | | |
| OH of serine | benzyl | $-CH_2-C_6H_5$ |
| -COOH of aspartate | | |
| -COOH of glutamate | t. butylmercapto | $-S-C(CH_3)_3$ |
| SH of cysteine | | |
| imidazole of histidine | tosyl | $-SO_2-C_6H_4-CH_3$ |
| -NH of arginine | | |
| -NH$_2$ of lysine | benzyloxycarbonyl | $-C(=O)-O-CH_2-C_6H_5$ |
| | formyl | -CHO |
| Indole of tryptophan | | |

FIGURE 3

DIAGNOSTIC METHOD AND COMPOSITION FOR EARLY DETECTION OF HIV INFECTION

This application if a continuation, of application Ser. No. 07/199,143 filed May 26, 1988.

BACKGROUND OF THE INVENTION

This invention relates to polypeptides that correspond to peptides encoded by the nef gene of strains of Human Immunodeficiency Virus (HIV). More particularly, this invention relates to natural and synthetic polypeptides, a diagnostic method for detecting antibodies to HIV strains in biological fluids, to a diagnostic kit for carrying out the method, and to vaccine compositions containing the polypeptides.

Acquired immune deficiency syndrome (AIDS) is a condition which is now of major importance in North America, Europe, and Central Africa. The casual agent of AIDS is believed to be a retrovirus. Recent estimates suggest that approximately 1 million Americans may have been exposed to the AIDS virus. The individuals affected show severe immunosuppression, which may be followed by the onset of fatal diseases. The transmission of the disease most frequently takes place through sexual contact, although people using narcotics intravenously also represent a high-risk group. Furthermore, a large number of individuals have been infected with this virus after receiving contaminated blood or blood products.

The isolation and characterization of the first retrovirus, known as LAV, was described in a paper by F. Barre-Sinoussi, et al. Science, 220:868-871 (1983). The use of some extracts of this virus, and more especially of some of its proteins, to detect antibodies against the virus is described in U.S. Pat. No. 4,708,818 issued to Dr. Luc Montagnier, et al.

Several isolates of the AIDS retrovirus were subsequently reported by different investigators and the isolates were referred to in the literature by different designations. It is now universally recognized that viruses previously denominated lymphadenopathy associated virus (LAV), immune deficiency associated virus (IDAV1 and IDAV2), human T-lymphotropic virus type III (HTLV-III), and AIDS related virus (ARV) are all variants of the same retrovirus. See, e.q., Nature, 313:636-637 (1985).

A subcommittee empowered by the International Committee on the Taxonomy of Viruses recently proposed that the AIDS retroviruses be officially designated as the "Human Immunonodeficiency Viruses," to be known in abbreviated form as "HIV." Isolates of human retroviruses with clear but limited relationship to isolates of HIV (for example, more than 20% but less than 50% nucleic acid sequence identity) are not be called HIV unless there are compelling biological and structural similiarities to existing members of the group.

Recently, another pathogenic human retrovirus, termed HIV-2 (formerly LAV-2), was recovered from West African patients with AIDS. HIV-2 infection is associated with an immunodeficiency syndrome clinically indistinguishable from that caused by the prototype AIDS virus, HIV-1. Clavel et al., New Eng. J. Med., 316:1180-1184 (1987). HIV-2 is related to but distinct from HIV-1 Guyader et al., Nature, 326:662-669 (1987).

Retroviruses genetically related and biologically similar to HIV have been isolated from subhuman primates. These retroviruses are designated as immunodeficiency viruses of the appropriate host species, such as simian immunodeficiency virus (SIV). SIV was first isolated from captive rhesus macaques (Macaca mulatta) at the New England Regional Primate Research Center (NERPRC). This was soon followed by a report of isolation of an SIV called STLV-III from African green monkeys. Extensive serologic cross-reactivity exists between HIV-2 and SIV.

Many of the HIV isolates analyzed have a distinct restriction map, even if recovered from the same place and time. Identical restriction maps have been observed for the first two isolates designated LAV and HTLV-3, and thus appear as an exception.

Although there is fairly wide genetic variability in the virus, the different HIV-1 strains isolated to date from American, European, Haitian, and African patients have certain common antigenic sites conserved on some proteins. This relationship has made it possible to use the prototype LAV strain as a source of antigens for detecting antibodies against all HIV-1 class viruses, in all people who carry them, regardless of their origin. Work to date has focused on the use of core proteins, envelope proteins and glycoproteins, transmembrane proteins, and fragments of these proteins as antigens in immunoassays for antibodies to HIV.

Nevertheless, the existence of multiple human immunodeficiency viruses, such as HIV-1 and HIV-2, presents a complex epidemiologic picture. Simple serologic tests that unambiguously distinguish among these retroviruses are essential for sorting out their patterns of transmission and pathogenesis. Immunoassays in which whole virus lysates are used as antigens have poor specificity due to partial cross-reactivity against conserved core antigens. Thus, there exists a need in the art for peptide antigens that have the inherent advantage of high specificity.

Moreover, there are compelling epidemiological considerations that make early detection of infection by the AIDS virus essential. Thus, for example, infection of an individual with the AIDS virus may be suspected because of the clinical symptoms manifested by the individual, but the infection may be in a very late stage before these symptoms are observed. Meanwhile, transmission of the disease may have taken place.

Finally, there is a common belief that an effective vaccine against HIV infection must be developed in order to stem the spread of the virus. Work is progressing on the development of a vaccine, but an effective vaccine has not yet been found.

In summary, there exists a need in the art for reagents, means, and methods for the detection of the AIDS virus and viruses associated with lymphadenopathies in general. The reagents, means, and methods should make it possible to detect different strains of HIV and their viral components from different isolates. Further, there is a need for reagents, means, and methods for the early detection of HIV infection. Moreover, there exists a need for pharmaceutical compositions capable of inhibiting or preventing infection of cells by HIV in vivo.

SUMMARY OF THE INVENTION

This invention aids in fulfilling these needs in the art. More particularly, this invention provides a purified polypeptide corresponding to a peptide encoded by the nef gene of HIV. The polypeptide of nef protein has an amino acid sequence substantially corresponding to at least one of the following sequences:

LYS PHE ASP ASP PRO HIS GLY GLU THR LEU VAL TRP GLU PHE ASP PRO LEU LEU ALA TYR SER TYR GLU ALA PHE ILE ARG TYR PRO GLU GLU PHE GLY HIS LYS, (A)

of nef protein of HIV-2 and serotypic variants thereof;

LYS PHE ASP ASP PRO HIS GLY GLU THR LEU VAL TRP GLU PHE ASP PRO LEU LEU ALA TYR SER TYR GLU ALA PHE ILE ARG TYR PRO GLU GLU PHE GLY HIS LYS SER GLY LEU PRO GLU GLU GLU TRP LYS ALA ARG LEU LYS ALA ARG GLY ILE PRO PHE SER, (B)

of nef protein of HIV-2 and serotypic variants thereof;

MET GLY GLY LYS TRP SER LYS SER SER VAL VAL GLY TRP PRO THR VAL ARG GLU ARG MET ARG ARG ALA GLU PRO ALA ALA ASP GLY VAL GLY ALA TYR CYS(acm), (C)

(p11) of nef protein of HIV-1 and serotypic variants thereof;

MET GLY GLY LYS TRP SER LYS SER SER VAL VAL GLY TRP PRO THR VAL ARG GLU ARG MET ARG ARG ALA GLU PRO ALA ALA ASP GLY VAL GLY ALA ALA SER ARG ASP LEU GLU LYS HIS GLY ALA ILE THR SER SER ASN THR ALA ALA THR ASN ALA ALA CYS(acm) ALA TRP LEU GLU ALA GLN GLU GLU GLU GLU, (D)

(p12) of nef protein of HIV-1 and serotypic variants thereof;

ALA SER ARG ASP LEU GLU LYS HIS GLY ALA ILE THR SER SER ASN THR ALA ALA THR ASN ALA ALA CYS(acm) ALA TRP LEU GLU ALA GLN GLU GLU GLU GLU, (E)

(p13) of nef protein of HIV-1 and serotypic variants thereof;

CYS(acm) VAL GLY PHE PRO VAL THR PRO GLN VAL PRO LEU ARG PRO MET THR TYR LYS ALA ALA VAL ASP LEU SER HIS PHE LEU LYS GLU LYS GLY GLY LEU GLU GLY LEU ILE HIS SER GLN ARG ARG GLN ASP ILE LEU, (F)

(p14) of nef protein of HIV-1 and serotypic variants thereof;

CYS(mebzl) GLY TYR PHE PRO ASP TRP GLN ASN TYR THR PRO GLY PRO GLY VAL ARG TYR PRO LEU THR PHE GLY TRP CYS(acm) TYR LYS LEU VAL PRO VAL GLU PRO ASP LYS VAL GLY GLU ALA ASN LYS GLY GLU ASN THR SER LEU LEU HIS PRO VAL, (G)

(p15) of nef protein of HIV-1 and serotypic variants thereof;

GLY MET ASP ASP PRO GLU ARG GLU VAL LEU GLU TRP ARG PHE ASP SER ARG LEU ALA PHE HIS HIS VAL ALA ARG GLU LEU HIS PRO GLU TYR PHE LYS ASN CYS(acm), (H)

(p16) of nef protein of HIV-1 and serotypic variants thereof;

CYS(acm) TYR LYS LEU VAL PRO VAL GLU PRO ASP LYS VAL GLU GLU ALA ASN LYS GLY GLU ASN THR SER LEU LEU HIS PRO VAL SER LEU HIS GLY MET ASP ASP PRO GLU ARG GLU VAL LEU GLU TRP ARG PHE ASP SER ARG LEU ALA PHE HIS HIS VAL ALA ARG GLU LEU HIS PRO GLU TYR PHE LYS ASN CYS(acm), (I)

(p17) of nef protein of HIV-1 and serotypic variants thereof;

CYS(acm) LYS GLY GLY LEU GLU GLY LEU ILE HIS SER GLN ARG ARG GLN ASP ILE LEU ASP LEU TRP ILE TYR HIS THR GLN GLY TYR PHE PRO ASP, (J)

(p18) of nef protein of HIV-1 and serotypic variants thereof; and

CYS(acm) ARG GLY GLY LEU GLU GLY MET PHE TYR SER GLU ARG ARG HIS LYS ILE LEU ASN ILE TYR LEU GLU LYS GLU GLU GLY ILE ILE ALA ASP, (K)

(p19) of nef protein of HIV-1 and serotypic variants thereof.

A polypeptide comprised of a combination of these amino acid sequences is also contemplated by this invention. The abbreviation "acm" means acetamidomethyl and the abbreviation "mebzl" means methylbenzyl.

This invention also encompasses a labeled polypeptide of the invention. Preferably, the polypeptide is capable of being immunologically recognized by human body fluid containing antibodies to HIV. The antigen can be labeled with an immunoassay label selected from the group consisting of radioactive, enzymatic, fluorescent, chemiluminescent labels, and chromphores.

An immunological complex between a polypeptide of the invention and an antibody recognizing the peptide is also provided. The immunological complex can also be labeled with an immunoassay label selected from the group consisting of radioactive, enzymatic, fluorescent, chemiluminescent labels, and chromophores.

This invention also provides an in vitro diagnostic method for the detection of the presence or absence of antibodies which bind to an antigen comprising a polypeptide of the invention. The method comprises contacting an antigen comprising at least one of the polypeptides of the invention with a biological fluid for a time and under conditions sufficient for the antigen and antibodies in the biological fluid to form an antigen-antibody complex and detecting the formation of the complex. The detecting step can further comprise measuring the formation of the antigen-antibody complex. The formation of the antigen-antibody complex is preferably measured by immunoassay based on Western Blot technique or ELISA (enzyme linked immunosorbent assay) or indirect immunofluorescent assay.

A diagnostic kit for the detection of the presence or absence of antibodies which bind to an antigen comprising at least one polypeptide of the invention is also provided. The kit contains antigen comprising at least one of the polypeptides and means for detecting the formation of immune complex between the antigen and the antibodies. The antigens and the means are present in an amount sufficient to perform the detection.

This invention further provides genomic nucleotides, such as RNA and cDNA, of HIV encoding the peptides of the invention. The nucleotide is in a purified form and has a sequence substantially coding for the peptide of the invention or for a portion of this sequence.

This invention provides a DNA sequence encoding for a polypeptide of the invention. The DNA has a sequence coding for a peptide of the invention or for a portion of the peptide. The DNA sequence is in a purified form. The invention also covers variants of the RNA and DNA sequences.

This invention also provides a probe consisting of a radionuclide bonded to a polynucleotide DNA sequence of the invention.

In addition, this invention provides a hybrid duplex molecule consisting essentially of a polynucleotide DNA sequence of the invention hydrogen bonded to a nucleotide sequence of complementary base sequence, such as DNA or RNA.

Also, this invention provides a process for selecting a nucleotide sequence coding for a polypeptide of the invention, or for a portion of such a nucleotide sequence, from a group of nucleotide sequences, which comprises the step of determining which of the nucleotide sequences hybridizes to a polynucleotide sequence of the invention. The nucleotide sequence can be a DNA sequence or an RNA sequence. The process can include the step of detecting a label on the polynucleotide sequence.

Finally, this invention provides monoclonal antibodies to each of the polypeptides of the invention, one monoclonal antibody type for each polypeptide.

The polypeptides of this invention are thus useful as a portion of a diagnostic composition for detecting the presence of antibodies and antigenic proteins associated with HIV. Similarly, the polynucleotides of the invention are useful for the detection of HIV nucleotides in materials, such as human body fluids and human tissue. Moreover, it has been discovered that this invention makes it possible to detect HIV infection in humans in an early stage. In addition, the polypeptides can be used to raise antibodies for detecting the presence of antigenic proteins associated with HIV. The peptides of the invention can also be employed to induce cellular immunity or to raise neutralizing antibodies that either inactivate the AIDS virus or reduce the viability of the virus in vivo or destroy infected cells. The ability to elicit virus-neutralizing antibodies is especially important when the polypeptides of the invention are used in vaccinating compositions.

BRIEF DESCRIPTION OF THE DRAWINGS

This invention will be more fully understood by reference to the drawings in which:

FIG. 2 depicts an amino acid sequence of the invention comprising 35 amino acids corresponding to an amino acid sequence encoded by the nef gene of HIV-2;

FIG. 3 depicts a sequence of the invention comprising 55 amino acids corresponding to an amino acid sequence encoded by the nef gene of HIV 2;

FIG. 5 depicts the amino acid sequences of nine other polypeptides of this invention;

FIG. 6 gives the structural formulas and chemical names of chemical groups that can be employed to protect moieties on amino acids used to prepare the polypeptides of the invention; and FIG. 7 shows a reaction mechanism for coupling amino acids with dicyclohexylcarbodiimide.

DETAILED DESCRIPTION OF PREFERRED EMBODIMENTS

Figure 1:
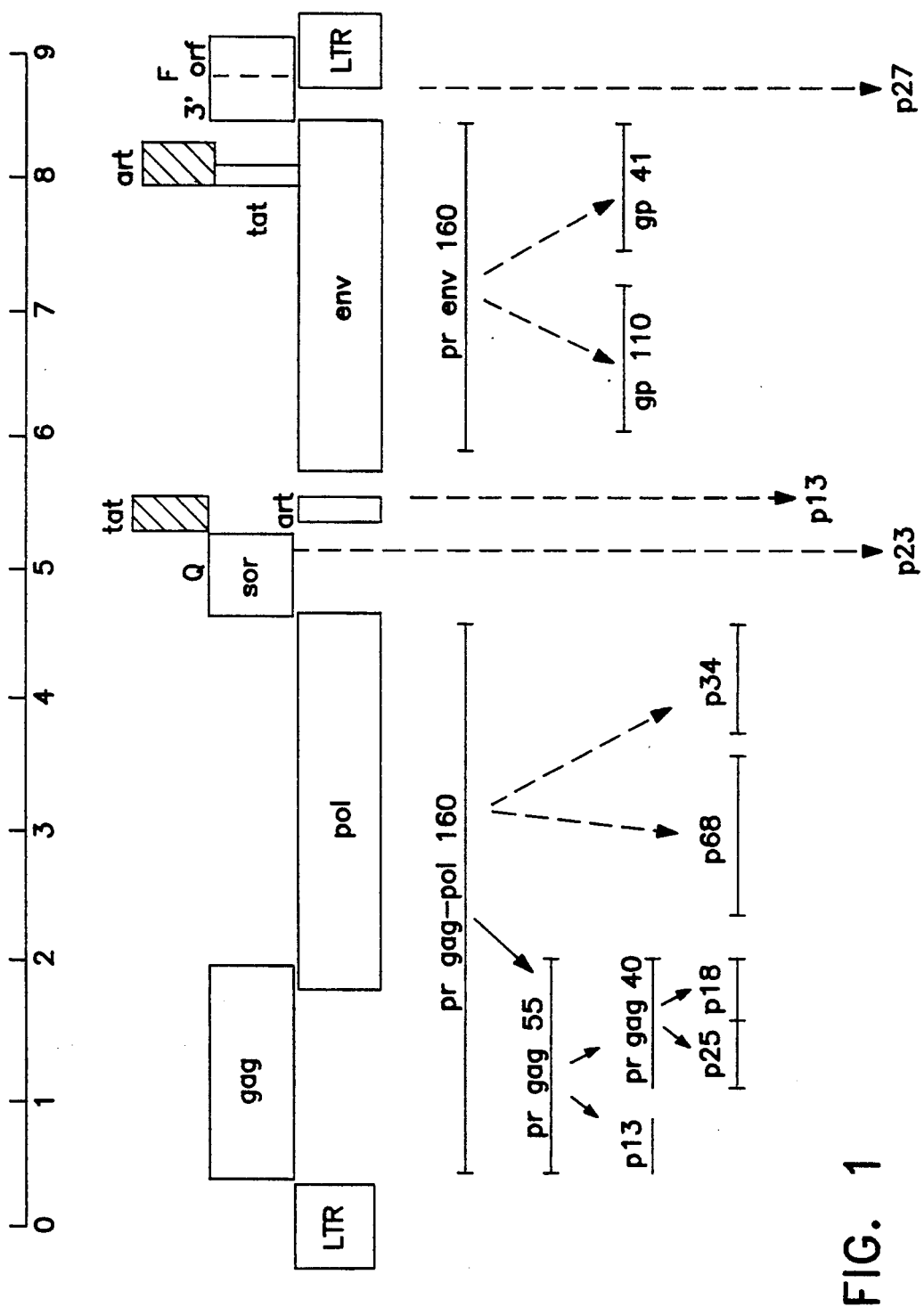
FIG. 1 is a map of the genome of the provirus of HIV-1.

In addition to the three portions of the genome found in all retroviruses and designated qaq, pol, and env, HIV isolates contain at least three other genes known as Q or Sor, TAT and F or 3' orf. Wain-Hobson et al., Cell 40:9-17 (1985); Arya et al., Proc. Natl. Acad. Sci. USA 83:2209-2213 (1986). For example, the genomic elements of the provirus of HIV-1 are shown in FIG. 1. Some of the proteins and glycoproteins encoded by several of the genes of the provirus are also shown in the Figure.

The nef gene has been referred to in the literature by different designations. For example, the nef gene is also known as the 3' orf or B gene. The F gene has also been referred to as the negative factor or nef gene.

The 3' open-reading frame nef gene of HIV and SIV is absent from most retroviral genomes. nef deficient HIV mutants show cytopathic effect in vitro and enhanced replication of virus. The nef (3' orf) gene encodes a polypeptide of 206 amino acids which can by myristylated at the N-terminal.

The nef gene product has been characterized by reaction with the sera of patients suffering from AIDS, and the identity of the protein has been confirmed by direct amino acid sequencing. Allan et el., Science 230:810-813 (1985). The nef protein is recognized by 30 to 90% of patients' sera. This protein migrates on an SDS-acrylamide gel according to an apparent molecular weight of between 26 and 28 kD. Some authors have demonstrated an nef gene product of between 24 and 25 kD, raising the possibility of an initiation of translation at a second ATG in the nef gene.

The nef protein is not glycosylated, although two potential N-glycosylation sites are present. It has been demostrated that the nef protein is acylated by myristic acid. Myristylation of nef protein at its N-terminal suggests it could be associated with the cell membrane. There is a tetrapeptide (Arg-Phe-Asp-Ser) in the nef protein which is found in certain proteins involved in cell adhesion, and also in one chain of the Class II HLA antigen.

One investigator raised the possibility that the nef protein plays a part in the recognition and attachment of the env protein and of the LAV virus to T4 lymphocytes, thereby contributing to the dissemination of the virus. Auffray, C.R. Acad. Sci, Paris 302; Series III, 287-292 (1986). The high variability )2 to 17%) of the nef protein from one strain to another, a variability comparable to that of the envelope glycoprotein, suggests that the nef protein effectively plays a part in infection. Rather et al., Nature 313:277-284 (1985).

The present invention provides amino acid sequences of various proteins of the nef gene of HIV retrovirus. More particularly, polypeptides of the invention have the amino acid sequences (A) through (L) described above. The amino acid sequences were determined from nef gene products. The following codes have been used to identify the amino acids:

| A | Ala | Alanine |
| --- | --- | --- |
| C | Cys | Cysteine |
| D | Asp | Aspartic Acid |
| E | Glu | Glutamic Acid |
| F | Phe | Phenylalanine |
| G | Gly | Glycine |
| H | His | Histidine |

| | | |
|---|---|---|
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The amino acid sequences of the polypeptides of the invention are shown in FIGS. 2-5. The amino acid sequences are shown in the Figures with the $NH_2$-termini nearest the left-hand margin and the COOH-termini nearest the right-hand margin.

More particularly, FIGS. 2 and 3 depict the amino acid sequences of polypeptides of the invention comprising 35 amino acids and 55 amino acids, respectively, corresponding to the amino acid sequences of polypeptides encoded by the nef gene of HIV-2.

Figure 4:
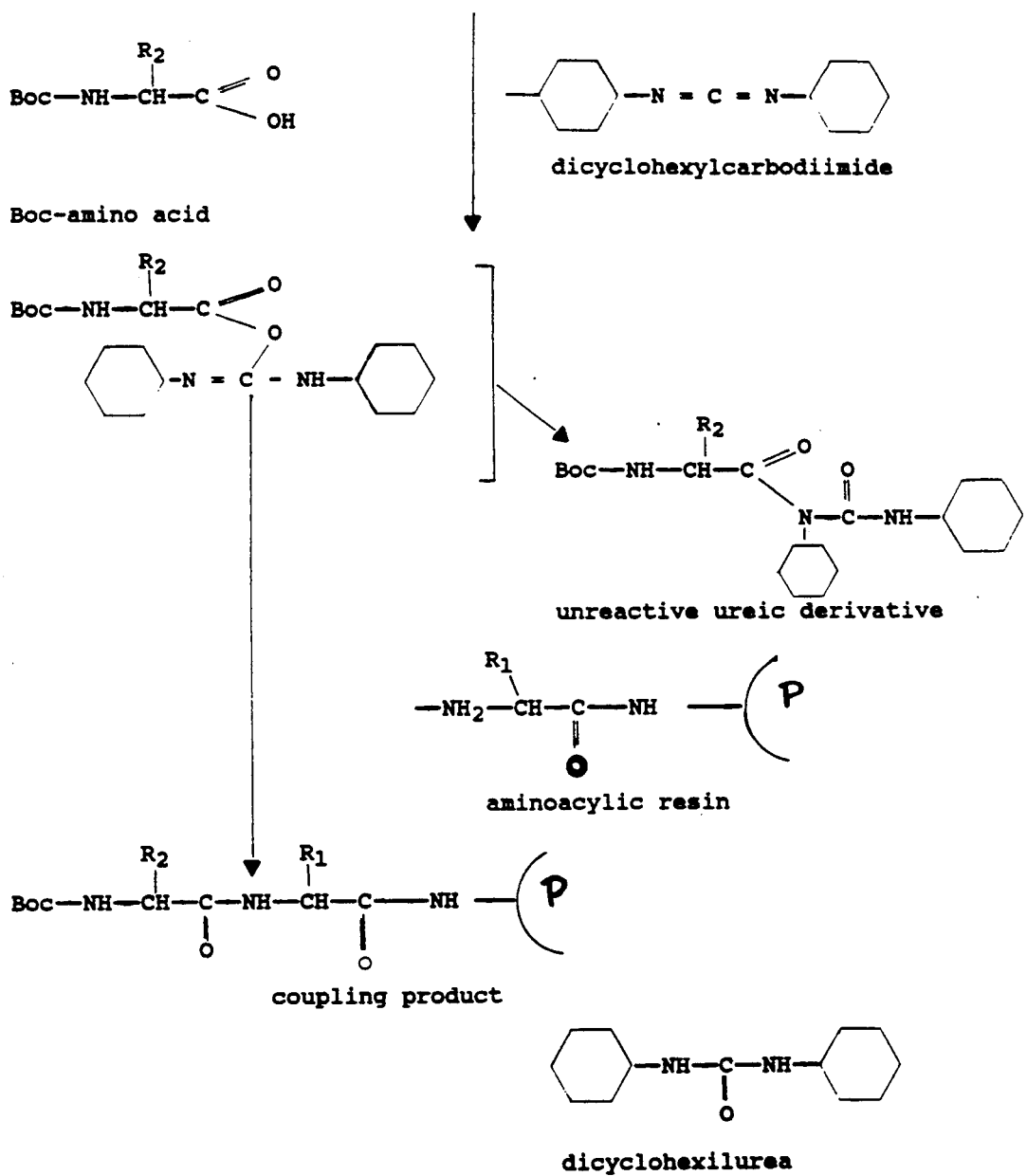
FIG. 4 depicts the amino acid sequences of polypeptides of HIV-1 of the invention in comparison with the amino acid sequences of polypeptides of HIV-2 of the invention.

The amino acid sequences of polypeptides of HIV-1 (LAV isolate) and polypeptides of HIV-2 (HIV-2$_{ROD}$ isolate) according to the present invention are aligned in FIG. 4. Gaps (-) are noted in the alignments shown in the Figure. Points of identity in the sequences are indicated by a colon (:). The top line in each case is the sequence of the polypeptide of HIV-2 and the bottom line is the sequence of the polypeptide of HIV-1.

FIG. 5 depicts similar polypeptides comprised of amino acids corresponding to the amino acid sequences of polypeptides encoded by the nef gene of HIV-1.

When the polypeptides of the invention are used as antigens for the detection of antibodies to HIV in human serum from an infected patient, antibodies to the polypeptides can be detected even though the patient does not test seropositive for the commonly used antigens, including p25, gp110, and gp41. The same patient may test seropositive for p25, gp110, and gp41 at a later time. These results suggest that HIV proteins or peptides having amino acid sequences corresponding to the amino acid sequences of the polypeptides of the invention are expressed in vivo before detectable amounts of p25, gp110, and gp41 are expressed. Thus, the polypeptides of the invention can be used in immunoassays for early detection of HIV infection in humans. The polypeptides of the invention are also useful for raising neutralizing antibodies in vivo against HIV infection in humans.

Several different polypeptides of the invention were examined for their reactivity with three different nef+ sera. The different peptides were diluted to a concentration of 2 mg/ml. On a strip of BIORAD paper for transblot tests, there were deposited different spots: 1 microliter (i.e. 1 ul), 2 microliters, 5 microliters, 10 microliters.

After drying, a classical Western Blot test was performed by using protein-nef-positive serums as antibodies in dilutions of 1/100, 1/200,- and 1/300. The polypeptides pF 11, pF 13, pF 14, pF 15, pF 16, pF 17, pF 18, pF 19 were tested. The positive results which were obtained with the three different anti-nef+ human sera are summarized in TABLE 1.

TABLE 1

Peptides Recognized by Three Anti-nef+ Sera

| | SERUMS | | | | | | | | | | | |
|---|---|---|---|---|---|---|---|---|---|---|---|---|
| | Chat 1/300 | | | | P.G. 1/200 | | | | 1545 1/200 | | | |
| PEPTIDES | 10 ul | 5 ul | 2 ul | 1 ul | 10 ul | 5 ul | 2 ul | 1 ul | 10 ul | 5 ul | 2 ul | 1 ul |
| pF16 | +++ | ++++++++++ | | | | — | — | — | ++ | — | — | — |
| pF19 | ++ | ++ | — | — | + | tr | — | — | + | + | — | — |
| pF13 | + | + | tr | — | — | — | — | — | tr | — | — | — |
| pF17 | — | — | — | — | — | — | — | — | tr | | | | tr = trace (weak reactions)
ul = microliter

It will be understood that the polypeptides of the invention encompass peptides having equivalent peptide sequences. By this it is meant that peptide sequences need not be identical to the sequences disclosed herein. Variations can be attributable to local mutations involving one or more amino acids not substantially affecting the immunogenic properties or antibody-binding capacity of the peptide. Variations can also be attributable to structural modifications that do not substantially affect immunogenic properties or antibody-binding capacity. Thus, for example, this invention is intended to cover serotypic variants of the polypeptides of the invention.

It will also be understood that the present invention is intended to encompass the polypeptides and peptide fragments thereof in purified form, whether or not glycosylated or myristylated, and whether obtained using the techniques described herein or other methods.

In a preferred embodiment of this invention, the polypeptides are free of human blood-derived proteins, such as human serum proteins, viral proteins, nucleotide sequences encoding these proteins, human tissue, and human tissue components. In addition, it is preferred that the polypeptides are free of other nucleic acids, extraneous proteins and lipids, and adventitious microorganisms, such as bacteria and viruses.

The polypeptides of the invention can be obtained by synthesis from the corresponding amino acids, by expression of the nef protein or polypeptide in a suitable procaryotic or eucaryotic cell by recombinant DNA technology, or from HIV infected cells. Since it is desirable to use very pure reagents in diagnostics and in pharmaceutical compositions, preparation of the polypeptides by chemical synthesis is preferred. More particularly, epitope-bearing polypeptides, particularly those whose N-terminal and C-terminal amino acids are free, are accessible by chemical synthesis using techniques well known in the chemistry of proteins. For example, the synthesis of peptides in homogeneous solution and in solid phase is well known. Following is a description of suitable procedures that can be employed.

A. SYNTHESIS, PURIFICATION AND CHARACTERIZATION OF PEPTIDES

1. Synthesis of peptides

The polypeptides of the invention can be prepared by Merrifield's method in the solid phase, which has been used successfully for many years. J. Am. Chem. Soc. 85:2149–2154 (1964). The principle is to bring together a solid phase on which the peptide sequence will be assembled and a liquid phase containing solvent and reagents. At each stage, the separation between the growing peptide and the reagents is achieved by simple filtration and washing operations.

Initially, a solid support carrying a reactive group X reacts with a carboxyl of an amino acid, which is introduced with its alpha-$NH_2$ blocked, in order to form a covalent bond. After unblocking of the amino function, a second protected amino acid is introduced to form the first peptide bond. By a succession of unblocking and coupling reactions, the synthesis progresses from the C-unit to the terminal N-unit. When the desired sequence has been assembled, the peptide is released from the solid phase by a specific reaction that results in cleavage of the initially formed peptide-resin bond.

Experimental aspect of the synthesis:

1. Nature of the solid support:

A good solid support must be:

insoluble in the solvents and reagents of the liquid phase;

- inert to the reagents used in the synthesis;

- sufficiently stable physically to be agitated and subjected to filtration;

- ensure excellent diffusion of the reagents in order not to slow the kinetics by too large a factor compared with those of reactions in solution.

Two kinds of resins are preferred:

- a resin which is obtained by copolymerization of styrene in the presence of 1% divinylbenzene, and the reactive function of which is an benzhydrylamine group (Ph-CHPh-$NH_2$); with substitution of 0.2 mmole $NH_2$/g of resin; or

- a macroporous polyacrylamide resin, the reactive function of which is the aminomethyl group (-$CH_2$-$NH_2$) containing 0.5 or 0.7 mmole $NH_2$/g.

2. Nature of the amino acids:

a. Protection of alpha-amino groups.

The alpha-$NH_2$ function of the added amino acid is protected to prevent autocondensation of the amino acids. The protective group used for this synthesis is the tert-butoxycarbonyl group (Boc), which is eliminated by 30% trifluoracetic acid (TFA) in dichloromethane (DCM).

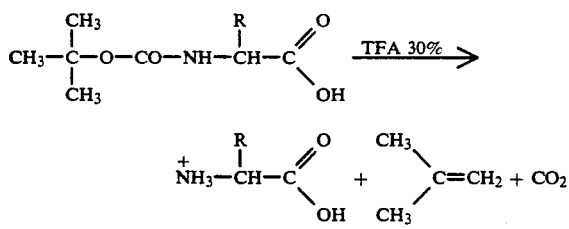

b. Protection of the side-chain functional groups.

In contrast to temporary protection of the alpha-amino functions, the functions carried by side chains of the amino acids must be kept protected throughout the entire synthesis, and consequently, the protective groups must be nonlabile in 30% TFA solution. On the other hand, they will generally be unblocked by hydrofluoric acid, the reagent used to cleave the peptide-resin bond. Examples of different protective groups for corresponding amino acids are listed in FIG. 6.

3. Experimental device.

Assembly of the peptides was performed automatically on an Applied Biosystems peptide synthesizer Model 430A.

4. Procedure for incorporation of an amino acid (aa) unit.

Table 2 describes the experimental procedure which permits a synthesis cycle to be effected.

TABLE 2

Procedure for Incorporation of a Unit

| Major Stages of Synthesis Cycle | Detailed Procedure |
|---|---|
| Unblocking of the amino functions | Two pretreatments of 2 min. followed by one treatment of 30 min. with 30% TFA/$CH_2Cl_2$. |
| Washing | Five times for 2 min. with $CH_2Cl_2$. |
| Neutralization | Two pretreatments of 2 min. followed by one treatment of 10 min. with 5% DIEA/$CH_2Cl_2$. |
| First coupling | 3-fold excess of Boc-aa and of DCC in $CH_2Cl_2$ (2 hours). |
| Washing | Five times for 2 min. with $CH_2Cl_2$. |
| Re-neutralization | Two pretreatments of 2 min. followed by one treatment of 10 min. with 5% DIEA/$CH_2Cl_2$. |
| Washing | Five times for 2 min. with $CH_2Cl_2$ and one time for 2 min. with DMF. |
| Second coupling | 1.5-fold excess of benzotriazole ester of the amino acid in DMF (1 hour). |
| Washing | Five times for 2 min. with $CH_2Cl_2$. |

More particularly, the synthesis involves:

Unblocking: The yield is generally not checked, since the conditions used are normally sufficient to achieve complete elimination of the Boc groups protecting the alpha-$NH_2$ functions.

Neutralization It is necessary in order to deionize the alpha-$NH_2$ amine of the peptide on the resin and to make it nucleophilic in order to participate in the coupling reaction.

- First coupling: The coupling agent is dicyclohexylcarbodimide (DCC), and the reaction mechanism is described in FIG. 7. The secondary reaction, which yields an unreactive ureic derivative, depends on the nature of the solvent: It is fairly slight in dichloromethane and is counterbalanced by the use of excess reagents (DCC and Boc-aa).

- Second coupling: After washing of the preceding reaction solution, reneutralization is effected in order to activate the alpha-amines which may have escaped the first basic treatment. The second coupling relies on the use of freshly prepared benzotriazole ester of Boc-aa. This coupling method was initially used for the incorporation of asparagine and of glutamine (Hruby et al., J. Med. Chem., 16:624 (1973)) which, in direct contact with DCC, yield a nitrile (Paul and Kende, J. Amer. Chem. Soc., 86:741 (1964)). A second coupling with hydroxybenzotriazole (HOBt) is effective for all the amino acids.

- Preparation of the benzotriazole ester of the Boc-amino acid: An equimolar mixture of DCC and HOBt in dimethylformamide (DMF) is prepared and left to incubate for ten minutes at 0° C. Thereafter, the Boc-amino acid is added and the reaction is continued at 0° C. for ten minutes. The benzotriazole ester of the Boc-amino acid formed in this way is added to the reaction vessel (Table 2).

5. Analytical checks during synthesis.

Because the synthesis proceeds without purification of the intermediates, it is imperative to check that the coupling reactions are complete. The diagram of FIG. 7 shows the importance of having complete coupling reactions for the synthesis of long sequences; if a 40-unit peptide is synthesized with an overall yield (unblocking, neutralization, and coupling) of 98%, a mixture containing 46% of the desired peptide and 54% of different shorter peptides is obtained. If the average yield per stage is 99%, the complete peptide will be present in 67% yield. If the yield is 99.5%, the desired peptide will then represent 82%, and only 18% of mixtures of shorter peptides.

Three simple coupling tests are available:.

- Ninhydrin test (Kaiser et al., Anal. Biochem., 34:595(1970)): An aliquot of peptidyl resin (around 10 mg) is removed and washed thoroughly with ethanol in small glass tubes. After centrifugation and elimination of the ethanol, a ninhydrin solution is added and allowed to react for 5 minutes at 95° C. The appearance of a blue coloration (positive test) indicates incomplete coupling. If the color of the resin does not change, coupling has reached at least 99% of completion.

- Fluorescamine test (Felix and Jimenez, Anal. Biochem., 52:377 (1973)),-which is slightly more sensitive than the ninhydrin test, permits detection of less than 1% of free NH2. An aliquot of peptidyl resin (10 to 20 mg) is washed successively with DCM, ethanol and 5% DIEA in DCM, after which the fluorescamine is added. The reaction takes place in a basic solution (5% DIEA) for 10 minutes. After washing and drying, the resin is viewed under a UV lamp at a wavelength of 366 nm. The appearance of fluorescence indicates the presence of free $NH_2$.

- Chloranil test (Christensen, Acta. Chem. Scand. B., 33:763 (1979)). After coupling of any amino acid with proline, the first two tests cannot be used because of their low sensitivity in the detection of secondary amines. Chloranil (2,3,5,6-tetrachlorobenzoquin-1,4-one) is used. To an aliquot of peptidyl resin (5 to 10 mg) there is added 200 microliter of acetone and 50 microliter of a saturated solution of chloranil in toluene, and the entire mixture is kept agitated for 5 minutes. The appearance of a green coloration indicates incomplete coupling. Depending on the test result, if it remains positive after a second or third coupling, the alpha-$NH_2$ functions which have not reacted are blocked by acetylation in order to prevent the formation of deficient peptide or, if it is negative, a new unblocking-coupling cycle is initiated. In addition, the quantity of amines present on the resin is titrated at regular intervals (every two or three units incorporated). This quantity must remain constant and equal to the quantity of amino acid initially fixed on the solid phase. The method of picric acid salts (Gisin, Helv. Chim. Acta., 58:241 (1972)) can be used: 10 to 20 mg of dried peptidyl resin is weighed accurately in a syringe and treated as follows:

- 5 washings with DCM;
- 3 treatments of 3 minutes with a picric acid solution (0.01 M in DCM);
- 5 washings with DMC to remove the excess picric acid;
- 5 treatments of 5 minutes with DIEA (5% in DCM), which displace the picrate bonded to the resin. The filtrates are collected in a 100-ml volumetric flask;
- Washing of the resin with ethanol, after which the flask is made up to 100 ml with ethanol;
- Measurement of the optical density at 358 nm: Knowing the value of the molar extinction coefficient at 358 nm (13,800), there is calculated the concentration of the free alpha-$NH_2$ groups which were able to react with the picric acid to form the corresponding salt.

6. Acetylation of the peptide on the resin.

Whether the coupling of an amino acid remains incomplete after several reaction attempts, or whether the synthesis of the peptide has been completed and it is desired to block the alpha-$NH_2$ end of the peptide by the acetyl group (acetylation of the terminal N is performed with the objective of having a peptide which, from the viewpoint of charge, simulates that which exists in native protein), the peptide on the resin is acetylated under the following conditions:

- neutralization by 5% DIEA;
- washings with DCM;
- washings with DMF; and
- acetylation by a mixture of 1 ml of acetic anhydride (10 mmole) and 1.7 ml of DIEA (10 mmole) in DMF. The reaction lasts for 20 to 30 minutes and is considered to be complete when the coupling test is negative.

7. Cleavage of the peptide-resin bond.

Cleavage of the bond between the peptide and the solid phase is effected by anhydrous hydrofluoric acid (HF) at 0° C. (Lenard and Robinson, J. Amer. Chem. Soc., 89:141 (1967) Sakaibara et al., Bull. Chem. Soc. Jap., 40:2164 (1967)). It is accompanied, if protective groups which are labile in HF were chosen, by the unblocking of the side chains. The presence of anisole (10% by volume) is necessary to trap the free radicals and thus to prevent the alkylation of certain units, such as tyrosine, by the liberated protective groups. By using a benzhydrylamine resin, the peptide is obtained in its C-alpha-amido form at the end of the reaction. After evaporation of the hydrofluoric acid, the anisole is extracted by ether and the peptide is solubilized by acetic acid. The yield of the cleavage reaction is calculated from the results of analyses of amino acids indicating the quantities of peptide before (peptide fixed to the resin) and after (free unpurified peptide) cleavage by the hydrofluoric acid. However, certain protective groups of the side chains of some amino acids, such as formyl-tryptophan, are removed only by an additional treatment.

8. Unblocking of tryptophan.

In the formyltryptophan form, the aromatic amino acid is suitably protected during the synthesis against the risks of oxidation of the indole group. This indole group can be regenerated by action of a base (1 M hydroxylamine, pH 9) for one hour in aqueous solution (Ohno et al., Bul. Chem. Soc. Japan, 45:2852 (1972)).

The polypeptides prepared by these chemical synthesis techniques can then be collected and employed in the practice of this invention.

The polypeptides of the invention can also be obtained from nef protein prepared by recombinant DNA techniques or recovered from infected cell cultures. For example, native nef protein can be subject to Edman degradation to obtain the polypeptides of the invention. When the polypeptide is obtained from infected cells, conventional purification techniques can be employed. For example, polypeptides can be separated from the live virus by centrifugation, and the polypeptides can then be purified by ultracentrifugation, gel filtration, ion-exchange chromatography, affinity chromatography, or by the use of monoclonal antibodies, or by combinations of these procedures.

It will be understood that the polypeptides of the invention can also comprise part of an expressed gene product or a portion of such a product. This can be accomplished by moving a transcript for the polypeptide into a bacterial expression system and making sufficient amounts of a fusion protein that can be used as an antigen.

The nef protein can be obtained by expression of a sequence coding for the protein in vaccinia virus (VV). The expression of a heterologous protein in vaccinia virus requires that the coding sequence be aligned with a promoter sequence of vaccinia and be inserted in a nonessential segment of the vaccinia DNA. This DNA, situated on both sides, permits recombination with the vaccinia genome in vivo by a double reciprocal recombination event which transfers the coding sequence and the accompanying promoter into the vaccinia genome. See Proc. Natl. Acad. Sci. USA 79:4927–4931 (1982); Proc. Natl. Acad. Sci. USA 79:7415–7419 (1982); and Proc. Natl. Acad. Sci. USA 80:5364–5368 (1983). A plasmid identified as plasmid pTG1147 was prepared in this way. E. coli transformed by pTG1147 deposited on Jun. 6 1986, at the Collection Nationale de Cultures de Microorganisms in Paris, France, under accession no. C.N.C.M. I-561. The transfer of the nef gene coding sequence and of the accompanying promoter into the vaccinia genome can be accomplished as follows.

The strategy described by Smith et al., in Proc. Natl. Acad. Sci. USA 80:7155–7159 (1983), rests on the in vivo exchange between a plasmid carrying an insert in a VVTK gene and the wild-type viral genome, so as to inactivate the TK gene carried by the virus. The TK viruses can be selected by plating on a cell line (TK negative) in the presence of 5-bromodeoxyuridine (5BUDR). Thymidine kinase phosphorylates the 5BUDR to 5'-monophosphate, which is then converted to triphosphate. This compound is a lower dTTP analog, and its incorporation into DNA blocks the correct development of the virus. A TK virus can nevertheless replicate its DNA normally, and it leads to viral plaques which are visible in a cell line which is also TK.

Vaccinia virus reproduces in the cytoplasm of infected cells rather than in their nucleus. For this reason, it is not possible to make use of the machinery for replication and transcription of the host's DNA, and it is necessary for the virion to possess the components for the expression of its genome. Purified VV DNA is non-infectious.

In order to generate the recombinants, it is necessary to perform the cellular infection with the VV virion simultaneously with a transfection with the cloned DNA segment which is of interest. However, the generation of the recombinants is limited to the small proportion of cells which are competent for transfection with DNA. For this reason, it is necessary to employ an indirect strategy of "congruence" in order to reduce the background due to the non-recombinant parent viruses. This can be accomplished by using, as live infectious virus, a temperature-sensitive (ts) mutant of vaccinia which is incapable of reproduction at a non-permissive temperature of 39.5° C. Virology 131:385–393 (1983).

When the cells are infected with a ts mutant under no permissive conditions and transfected with the DNA of a wild-type virus, viral multiplication will take place only in the cells which are competent for transfection and in which a recombination between the wild-type DNA and genome of the ts virus has taken place; no virus will multiply in the other cells, in spite of the fact that they have been infected. If a recombinant plasmid containing a vaccinia DNA fragment, such as pTG1147, is included in the transfection mixture, at the appropriate concentration, with the wild-type DNA, it is also possible to procure its participation in the homologous recombination with the vaccinia DNA in the competent cells.

Specifically, monolayers of primary cells of chick embryo fibroblasts (CEF) can be infected at 33° C. with VV-Copenhagen ts7 (0.1 pfu/cell) and transfected with a calcium phosphate coprecipitate of the DNA of the VV-Copenhagen wild-type virus (50 ng/$10^6$ cells) and the recombinant plasmid (50 ng/$10^6$ cells). After incubation for 2 hours at a temperature which does not permit the growth of the ts virus (39.5° C.), the cells can again incubated for 48 hours at 39.5° C. Dilutions of ts+ virus can be used for reinfecting a monolayer of 143B-TK human cells at 37° C., which are then incubated in the presence of 5BUDR (150 ug/ml). Various plaques of TK virus are obtained from these cells which have received the recombinant plasmid, while the control cultures without plasmid do not show visible plaques. The TK viruses can then be subcloned by means of a second selection in the presence of 5BUDR.

A correct double reciprocal recombination event between the hybrid plasmid pTG1147 and the VV genome leads to the exchange of the TK gene carrying the insert with the TK gene of the virus, the recombinants thereby becoming TK. The DNAs can be purified from the different TK recombinant viruses, digested with HindIII, and subjected to agarose gel electrophoresis. The DNA fragments can be transferred onto a nitrocellulose filter according to the technique described by Southern. The filter can then be hybridized with plasmid pTG1147, nick-translated with $^{32}P$. After the filter has been washed, the latter fluorographed bands are visible on the autoradiograph when the vaccinia virus has incorporated the nef gene of the LAV. One of these recombinants can be employed for nef protein synthesis.

For example, in order to demonstrate the expression of the nef gene of LAV using the hybrid vaccinia virus, BHK21 rodent cells, which are cultured in a G-MEM medium +10% fetal calf serum, were infected with a recombinant identified as VV.TG.FLAV.1147. A fresh semi-confluent monolayer ($10^6$ cells) was infected with 0.2 pfu/cell and incubated for 18 hours. The medium was then removed, and a medium having a low methionine content and supplemented with 10 ug/ml of [$^{35}S$]methionine (5 mCi/300 ug) was (1 ml per $10^6$ cells). The cells were incubated at 37° C. and labelled proteins were collected by centrifugation. Aftter separation into pellet and supernatant, the proteins were incubated with a serum belonging to patients suffering from AIDS. The proteins which react with the serum were recovered by adsorption on a protein A-Sepharose resin, spread by electrophoresis on an SDS-polyacrylamide gel, and autoradiographed according to a technique described by Lathe et al., Nature 284:473–474 (1980). The autoradiographs showed that some sera of patients suffering from AIDS specifically bind two proteins of the infected cell extracts. The apparent molecular weights of 25.5 and 27 kD suggested equivalence with the nef protein identified by the sera of patients suffering from AIDS in an authentic nef protein preparation and in extracts of cells infected with the LAV virus.

The recombinant techniques just described are discussed in greater detail in copending U.S. application Ser. No. 162,328, filed Feb. 5, 1988, by Marie-Paule Kieny, Bruno Guy, Jean-Pierre Lecoq, and Luc Montagnier, for VACCINE CONTAINING THE PROTEIN F OF THE AIDS VIRUS, which is based on PCT/FR87/00219, filed Jun. 15, 1987, which in turn is based on French Published Application No. 2 600 079, published Dec. 18, 1987. The entire disclosure of the copending U.S. application is relied upon and incorporated herein by reference.

This invention also includes polypeptides in which a portion of the polypeptide of the invention containing an antigenic binding site is linked to a larger carrier molecule, such as another polypeptide or a protein, and in which the resulting product exhibits specific binding for antibodies to HIV in vivo or in vitro. In this case, the resulting polypeptide can be smaller or larger than the polypeptide of the invention.

For polypeptide sequences of less than about 20 amino acids, it may be advantageous to covalently couple or conjugate the polypeptide to a physiologically acceptable, non-toxic carrier molecule in order to increase immune response in vivo. By way of examples of carrier molecules or macromolecular supports which can be used for making conjugates according to the invention, mention can be made of natural proteins, such as tetanoic toxoid ovalbumin; serum albumins, such as bovine plasma albumin; and hemocyanins, such as keyhole limpet hemocyanin (KLH). Synthetic macromolecular carriers, for example polysines or poly(D-L-alanine)-poly(L-lysine)s, can also be employed. Other types of macromolecular carriers which can be employed generally have molecular weights higher than about 20,000 daltons and are known from the literature. Polypeptide-ovalbumin conjugates are especially useful for microtiter assays, and polypeptide-sepharose conjugates can be used for purifying antibodies.

The polypeptides of the invention can be attached to the carrier molecule using conventional techniques. For instance, glutaraldehyde can be employed to couple amino groups on the polypeptide to amino groups on the carrier molecule. Maleimidobenzoyl-N-hydroxysuccinimide ester is a useful reagent for attaching polypeptides by way of a terminally situated cysteine residue. The diazotizing reagent bis-diazobenzidine can be used to attach the side chain of a tyrosine in the polypeptide to tyrosine groups in the carrier. Also, water-soluble carbodiimides can be used for carboxyl-to-amino coupling with appropriate blocking and unblocking as needed.

The polypeptides and the polypeptide fragments of the present invention can be used to identify antibodies to HIV in materials and to determine the concentration of the antibodies in those materials. Thus, the polypeptides and polypeptide fragments can be used as antigens for qualitative or quantitative determination of the retrovirus in a material. Such materials of course include biological fluids, such as human body fluids, including human sera. When used as a reagent in an immunoassay for determining the presence or concentration of the antibodies to the retrovirus, the antigens of the present invention provide an assay that is convenient, rapid, sensitive, and specific.

More particularly, the antigens of the invention can be employed for the detection of HIV by means of immunoassays that are well known for use in detecting or quantifying humoral components in fluids. Thus, antigen-antibody interactions can be directly observed or determined by secondary reactions, such as precipitation or agglutination. Other immunoassays in which the antigens of the present invention can be employed include, but are not limited to, radioimmunoassay, competitive immunoprecipitation assay, enzyme immunoassay, and immunofluorescence assay. It will be understood that tubidimetric, colorimetric, and nephelometric techniques can be employed.

Immunoassays can be carried out by immobilizing one of the immunoreagents, either an antigen of the invention or the antibodies to the antigen, on a carrier surface while retaining immunoreactivity of the reagent. The reciprocal immunoreagent can be unlabeled or labeled in such a manner that immunoreactivity is also retained. These techniques are especially suitable for use in enzyme immunoassays, such as enzyme linked immunosorbent assay (ELISA) and competitive inhibition enzyme immunoassay (CIEIA). An immunoassay based on Western Blot technique is particularly preferred.

When either the antigen of the invention or antibody to the antigen is attached to a solid support, the support is usually a glass or plastic material. Plastic materials molded in the form of plates, tubes, beads, or disks are preferred. Examples of suitable plastic materials are polystyrene and polyvinyl chloride. If the immunoreagent does not readily bind to the solid support, a carrier material can be interposed between the reagent and the support. Examples of suitable carrier materials are proteins, such as bovine serum albumin, or chemical reagents, such as gluteraldehyde or urea. Coating of the solid phase can be carried out using conventional techniques.

Depending on the use to be made of the polypeptides and antigens of the invention, it may be desirable to label the polypeptides and antigens. Examples of suitable labels are radioactive labels, enzymatic labels, fluorescent labels, chemiluminescent labels, and chromophores. The methods for labeling polypeptides and antigens of the invention do not differ in essence from those widely used for labeling immunoglobulin. The need to label may be avoided by using labeled antibody to the antigen of the invention or anti-immunoglobulin to the antibodies to the antigen as an indirect marker.

The polypeptides and antigens of the invention can be purified according to conventional techniques. For example, purification can be carried out by employing differences in molecular weights. Differential migration on a gel or gradient centrifugation can be employed. The antigens according to the invention can be purified by their affinity for lectins. The lectin can be immobilized on a solid support.

A more thorough purification of the antigens can be performed by immunoprecipitation with the sera of patients known to possess antibodies effective against the polypeptide, with concentrated antibody preparations, such as polyclonal antibodies, or with monoclonal antibodies directed against the antigen of the invention.

The invention provides immunogenic polypeptides, and more particularly, protective polypeptides for use in the preparation of vaccine compositions against HIV. These polypeptides can thus be employed as viral vaccines by administering the polypeptides to a mammal susceptible to HIV infection. Conventional modes of administration can be employed. For example, administration of the polypeptides can be carried out by oral, respiratory, or parenteral routes. Intradermal, subcutaneous, and intramuscular routes of administration are preferred when the vaccine is administered parenterally.

The ability of the polypeptides and vaccines of the invention to induce protective levels of neutralizing antibody in a host can be enhanced by emulsification with an adjuvant, incorporation in a liposome, coupling to a suitable carrier, or by combinations of these techniques. For example, the polypeptides of the invention can be administered with a conventional adjuvant, such as aluminum phosphate and aluminum hydroxide gel, in an amount sufficient to potentiate humoral or cell-mediated immune response in the host. Similarly, the polypeptides can be bound to lipid membranes or incorporated in lipid membranes to form liposomes that mimic the original HIV virion. The use of nonpyrogenic lipids free of nucleic acids and other extraneous matter can be employed for this purpose. Further, polypeptides of the invention which function as haptens can be chemically coupled to a carrier, such as a protein, in order to render the polypeptide more immunogenic. Of course, the carrier protein should be one that does not induce clinically significant hypersensitivity in the host. The polypeptide of the invention can be coupled to a protein carrier using the techniques previously described.

The immunization schedule will depend upon several factors, such as the susceptibility of the host to infection and the age of the host. A single dose of the vaccine of the invention can be administered to the host or a primary course of immunization can be followed in which several doses at intervals of time are administered. Subsequent doses used as boosters can be administered as needed following the primary course.

The polypeptides and vaccines of the invention can be administerd to the host in an amount sufficient to prevent or inhibit HIV infection in vivo. In any event, the amount administered should be at least sufficient to protect the host against substantial immunosuppression, even though HIV infection may not be entirely prevented. The polypeptides and vaccines of the invention can be administered together with a physiologically acceptable carrier. For example, a diluent, such as water or a saline solution, can be employed.

The nucleotide sequences of the peptides of the invention were derived by dideoxynucleotide sequencing. The base sequences of the nucleotides are written in the 5'→3' direction. Each of the letters shown is a conventional designation for the following nucleotides:

| | |
|---|---|
| A | Adenine |
| G | Guanine |
| T | Thymine |
| C | Cytosine. |

The polynucleotides of the invention can be prepared by the formation of 3'→5' phosphate linkages between nucleoside units using conventional chemical synthesis techniques. For example, the well-known phosphodiester, phosphotriester, and phosphite triester techniques, as well as known modifications of these approaches, can be employed. Deoxyribonucleotides can be prepared with automatic synthesis machines, such as those based on the phosphoramidite approach. Oligo- and polyribonucleotides can also be obtained with the aid of RNA ligase using conventional techniques.

The polynucleotides of the invention are in a purified form. For instance, the polynucleotides are free of human blood-derived proteins, human serum proteins, viral proteins, nucleotide sequences encoding these proteins, human tissue, and human tissue components. In addition, it is preferred that the polynucleotides are free of other nucleic acids, extraneous proteins and lipids, and adventitious microorganisms, such as bacteria and viruses.

The polynucleotides of the invention can be used as probes for the detection of a nucleotide sequence in a biological material, such as tissue or body fluids. The polynucleotide probe can be labeled with an atom or inorganic radical, most commonly using a radionuclide, but also perhaps with a heavy metal. Radioactive labels include $^{32}P$, $^{3}H$, $^{14}C$, or the like. Any radioactive label can be employed, which provides for an adequate signal and has sufficient half-life. Other labels include ligands that can serve as a specific binding member to a labeled antibody, fluorescers, chemiluminescers, enzymes, antibodies which can serve as a specific binding pair member for a labeled ligand, and the like. The choice of the label will be governed by the effect of the label on the rate of hybridization and binding of the probe to the DNA or RNA. It will be necessary that the label provide sufficient sensitivity to detect the amount of DNA or RNA available for hybridization.

When the polynucleotides of the invention are used as probes for hybridizing to a gene, the gene is preferably affixed to a water insoluble solid, porous support, such as nitrocellulose paper. Hybridization can be carried out using labeled polynucleotides of the invention and conventional hybridization reagents. The particular hybridization technique is not essential to the invention.

The amount of labeled probe which is present in the hybridization solution will vary widely, depending upon the nature of the label, the amount of the labeled probe which can reasonably bind to the filter, and the stringency of the hybridization. Generally, substantial excesses of the probe over stoichiometric will be employed to enhance the rate of binding of the probe to the fixed DNA.

Various degrees of stringency of hybridization can be employed. The more severe the conditions, the greater the complementary that is required for hybridization between the probe and the polynucleotide for duplex formation. Severity can be controlled by temperature, probe concentration, probe length, ionic strength, time, and the like. Conveniently, the stringency of hybridization is varied by changing the polarity of the reactant solution. Temperatures to be employed can be empirically determined or determined from well known formulas developed for this purpose.

This invention of course includes variants of the nucleotide sequences encoding the polypeptides of the invention or serotypic variants of the polypeptides of the invention exhibiting the same immunological reactivity as the polypeptides of the invention.

Although serologic assays directed to viral antigens identify persons with prior exposure to HIV-1, they do not specifically determine current infection. This phenomenon occurs because HIV can establish persistent infection without actively producing virus particles. While HIV infection can also be determined by isolating the virus from an HIV-1-seropositive person, HIV-1 lation involves prolonged cocultivation of peripheral blood mononuclear cells (PBMCs) with phytohemagglutinin (PHA)-stimulated lymphocytes from an uninfected donor or with a susceptible uninfected indicator cell line. The procedure can take up to three to four weeks and lacks sensitivity in that viruses cannot be consistently isolated from persons with documented infections. The nucleotide sequences of the present invention can be employed in a DNA amplification process known as the "polymerase chain reaction (PCR), which is useful for amplifying specific regions of HIV-1 proviruses. See, e.g., S. Kwok et al., J. Virol., 61:1690–1694 (1987). PCR is advantageous because this technique takes less than three days to complete.

More particularly, the HIV-1 antibody status of patients can be initially determined by an enzyme-linked immunosorbent assay (ELISA) and subsequently confirmed by Western Blot testing. Sera and PBMCs can be collected from seronegative patients (or seropositive patients for confirmatory testing), and the PBMCs can be processed to isolate DNA. The presence of HIV-1 in pBMCs can be monitored by the appearance of reverse transcriptase activity in PBMCs cocultivated with PHA-stimulated lymphocytes from healthy seronegative donors.

DNA primer pairs of known sequence positioned 10–300 base pairs apart that are complementary to the plus and minus strands of the DNA to be amplified can be prepared by well known techniques for the synthesis of oligonucleotides. One end of each primer can be extended and modified to create restriction endonuclease sites when the primer is annealed to the PBMC DNA. The PCR reaction mixture can contain the PBMC DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the PBMC DNA at an elevated temperature, cooling of the reaction mixture, and polymerization with the DNA polymerase.

Amplified sequences can be detected by the use of a technique termed oligomer restriction (OR). See, R.K. Saiki et al., Bio/Technology 3:1008–1112 (1985). For example, after amplification, a portion of the PCR reaction mixture can be separated and subjected to hybridization with an end-labeled nucleotide probe, such as a $^{32}P$ labelled adenosine triphosphate end-labelled probe. In OR, an end-labeled oligonucleotide probe hybridizes in solution to a region of the amplified sequence and, in the process, reconstitutes a specific endonuclease site. Thus, hybridization of the labelled probe with the amplified HIV viral sequence yields a double-stranded DNA form that is sensitive to selective restriction enzyme digestion. After restriction with an endonuclease, the resulting samples can be analyzed on a polyacrylamide gel, and autoradiograms of the portion of the gel with the diagnostic labelled fragment can be obtained. The appearance of a diagnostic fragment (e.g. 10-15 bases in length) in the autoradiogram indicates the presence of HIV-1 proviral sequences in the PBMCs.

Since a patient may have been infected with HIV-1 containing genetic variations or deletions in the regions targeted for amplification, the PCR technique using a single primer pair may not produce reliable results. Specifically, such variation could result in inefficient primer or probe binding, or elimination of specific restriction endonuclease sites, or both of these problems. For this reason, the PCR technique is preferably carried out with several primer pairs and probes derived from highly conserved regions of the viral genome, such as the LTR, qao, and env regions of HIV-1.

Since it may be possible to increase the sensitivity of detection by using RNA instead of chromosomal DNA as the original template, this invention contemplates using RNA sequences that are complementary to the DNA sequences described herein. The viral RNA can be converted to complementary DNA with reverse transcriptase and then subjected to DNA amplification. Increased sensitivity should result from the higher number of virus-specific RNA molecules than proviral DNA in infected cells. The use of RNA as the initial template and su sequent amplification is possible if the HIV-1 provirus in an infected PBMC is biologically active. See, Chin-Yih Ou et al., Science 239:295:297 (1988).

The PCR technique useful for determining whether seropositive or seronegative persons have detectable levels of HIV-1 provirus. Thus, this invention makes it possible to ut lize the PCR technique in complementing or replacing virus isolation as a routine means of determining the presence of HIV-1.

In summary, peptides encoded by nef gene of the genomes of variants of HIV have now been identified, the peptides have been sequenced, and the peptides have been synthesized. In addition to providing useful tools for detection of antibodies to the retrovirus in humans and for raising neutralizing antibodies to HIV in vivo, this invention adds to the base of knowledge relating to immunodeficiency active proteins and peptides of the AIDS virus.

What is claimed is:

1. An in vitro diagnostic method for the diagnosis of HIV infection by the detection of the presence or absence of antibodies that bind to an antigen of HIV, wherein said method comprises:

containing said antigen with a biological sample, wherein the biological sample is not seropositive for gag and env proteins of HIV, for a time and under conditions sufficient for the antigen and antibodies in the biological sample to form an antigen-antibody complex; and detecting the formation of the complex; wherein said antigen consists essentially of a peptide having the amino acid sequence:

MET GLY GLY LYS TRP SER LYS SER
SER VAL VAL GLY TRP PRO
THR VAL ARG GLU ARG MET ARG ARG
ALA GLU PRO ALA ALA ASP
GLY VAL GLY ALA ALA SER ARG ASP
LEU GLU LYS HIS GLY ALA
ILE THR SER SER ASN THR ALA ALA
THR ASN ALA ALA CYS (acm)
ALA TRP LEU GLU ALA GLN GLU GLU GLU GLU,
(pF12) of nef protein of HIV-1.

2. The method of claim 1, wherein said gag or env proteins are selected from the group consisting of p25, gp110, and gp41 of HIV.

3. The method of claim 1 or 2, wherein the detecting step further comprises measuring the formation of said antigen-antibody complex.

4. The method of claim 1 or 2, wherein said antigen is labeled with an immunoassay label selected from the group consisting of a radioisotope, an enzyme, a fluorescent label, a chemiluminescent label, and a chromphore.

5. The method of claim 1 or 2, wherein the detecting step employs a process selected from the group consisting of Western blot, enzyme linked immunosorbent assay (ELISA), and indirect immunofluorescent assay.

* * * * *

UNITED STATES PATENT AND TRADEMARK OFFICE
CERTIFICATE OF CORRECTION

PATENT NO. : 5,221,610
DATED : June 22, 1993
INVENTOR(S) : Montagnier et al.

It is certified that error appears in the above-indentified patent and that said Letters Patent is hereby corrected as shown below:

Title page, column 1, full address of first inventor, change "Robinson" to --Le Plessis Robinson--.

Claim 1, column 20, line 36, change "containing" to --contacting--.

Signed and Sealed this

Nineteenth Day of April, 1994

Attest:

BRUCE LEHMAN

*Attesting Officer*     *Commissioner of Patents and Trademarks*